United States Patent
Salimian (10) Patent No.: US 6,238,622 B1
(45) Date of Patent: May 29, 2001

(54) FLAME IONIZATION DETECTOR

(75) Inventor: Shahram M. Salimian, Westminster, CA (US)

(73) Assignee: Rosemount Analytical Inc., Anaheim, CA (US)

( * ) Notice: Subject to any disclaimer, the term of this patent is extended or adjusted under 35 U.S.C. 154(b) by 0 days.

(21) Appl. No.: 08/986,045

(22) Filed: Dec. 5, 1997

(51) Int. Cl.[7] .......................... G01N 30/68; G01N 31/12
(52) U.S. Cl. ................................ 422/54; 422/80; 422/98; 436/154
(58) Field of Search .................. 422/54, 98, 58, 422/59, 80; 436/154

(56) References Cited

U.S. PATENT DOCUMENTS

| | | | |
|---|---|---|---|
| 3,751,230 | * 8/1973 | Hofmann | 23/254 |
| 3,767,363 | * 10/1973 | Hofmann | 23/254 |
| 3,943,766 | 3/1976 | Delany | 73/341 |
| 3,973,792 | * 8/1976 | Gonner | 285/341 |
| 3,984,205 | * 10/1976 | Karas | 23/254 |
| 3,985,509 | * 10/1976 | Trone | 23/254 |
| 4,182,740 | * 1/1980 | Hartmann | 422/54 |
| 4,201,550 | 5/1980 | Noszticzius et al. | 23/242 |
| 4,211,746 | 7/1980 | Mees | 422/54 |
| 4,215,090 | 7/1980 | Dixon | 422/54 |
| 4,346,055 | 8/1982 | Murphy et al. | 422/54 |
| 4,410,854 | * 10/1983 | Kronesian | 324/468 |
| 4,555,930 | 12/1985 | Leach et al. | 73/23 |
| 4,599,218 | * 7/1986 | Demaison | 422/61 |
| 4,965,048 | 10/1990 | Ogasawara | 422/54 |
| 5,073,753 | 12/1991 | Collings et al. | 324/468 |
| 5,174,959 | * 12/1992 | Kundu | 422/59 |
| 5,227,135 | * 7/1993 | Godec | 422/98 |
| 5,576,626 | * 11/1996 | Lo | 324/464 |
| 5,728,586 | * 3/1998 | Platzer | 436/153 |

OTHER PUBLICATIONS

Brochure, "Model 7750—Process Gas Chromatograph," Rosemount Analytical, Feb. 1997.
Brochure, "Model 6750U—Process Gas Chromatograph Upgrade Kit," Rosemount Analytical, May 1997.
Brochure, "NGA 2000—McFID Methane, Non–Methane Hydrocarbon Analyzer," Rosemount Analytical, Feb. 1997.
Brochure, "Gas Analyzer Systems," Rosemount Analytical, 1997.
"Approval STandard Intrinsically Safe Apparatus and Associate Apparatus for Use in Class I, II and III, Division 1 Hazardous (Classified) Locations", Oct. 1988.
"Classification of Gases, Vapors, and Dusts for Electrical Equipment in Hazardous (Classified) Locations," *NFPA*, 1991.

* cited by examiner

*Primary Examiner*—Jill Warden
(74) *Attorney, Agent, or Firm*—Westman, Champlin & Kelly, P.A.

(57) ABSTRACT

A flame ionization detector burner, includes a housing having a generally cylindrical flame cavity therein extending along a generally longitudinal axis of the housing and a housing exterior with intake passageways communicating between the housing exterior and the flame cavity for passing fuel, air and sample flows into the flame cavity and an exhaust passage communicating between the housing exterior and the flame cavity for passing exhaust gasses out of the flame cavity. A burner carried in the housing cavity receiving the fuel, air, and sample flow generates a flame to ionize the sample. An ion collector plate spaced away from the burner carried in the time cavity collects sample ions and provides an electrical output representative of the sample ions to the housing exterior via an electrical feedthrough between the flame cavity and the housing exterior. The housing includes at least two cylindrical sidewalls removably joined together along the general longitudinal axis of the housing.

26 Claims, 6 Drawing Sheets

FLAME IONIZATION DETECTOR

BACKGROUND OF THE INVENTION

The present invention relates to instruments used to evaluate selected components of a chemical sample. More specifically, the present invention relates to a flame ionization detector.

Flame ionization detectors are typically used to analyze hydrocarbon components in a sample taken from a source such as exhaust from an industrial smoke stack, an automobile engine during its testing or adjustment, and high purity gasses during their production and testing.

A flame ionization detector burner typically includes a housing with a flame cavity with intake passageways and an exhaust passageway. Inside the flame cavity there is a burner that receives fuel, air, and a sample to create a flame to ionize the samples. An ionization collector plate collects the ions and produces a signal. representative of the concentration of sample ions. Flame ionization detectors burners are often located in hazardous locations where flammable vapors are present in which the flame ionization detector is required to meet hazardous location approvals. Flame ionization detector burners are also often incorporated into other instruments such as hydrocarbon analyzers or gas chromatographs.

Flame ionization detector burners are composed of a variety of components that often require seals and can be complex and expensive to manufacture and service. Flame ionization detectors have constraints that limit flame stability resulting in reduced accuracy.

Additionally, flame ionization detector burners have thermal constraints that limit the proximity of their installation near heat sensitive components such as instrumentation.

For the foregoing reasons there is a need for a flame ionization detector that is simpler to manufacture, has improved flame stability, and has reduced thermal constraints.

SUMMARY OF THE INVENTION

A flame ionization detector burner, includes a housing having a generally cylindrical flame cavity therein extending along a generally longitudinal axis of the housing and a housing exterior with intake passageways communicating between the housing exterior and the flame cavity for passing fuel, air and sample flows into the flame cavity and an exhaust passage communicating between the housing exterior and the flame cavity for passing exhaust gasses out of the flame cavity. A burner carried in the housing cavity receives the fuel, air, and sample flow and generates a flame to ionize the sample. An ion collector plate spaced away from the burner carried in the flame cavity collects sample ions and provides an electrical output representative of the sample ions to the housing exterior via an electrical feedthrough between the flame cavity and the housing exterior. The housing further comprises at least two cylindrical sidewalls removably joined together along the general longitudinal axis of the housing.

DETAILED DESCRIPTION OF THE PREFERRED EMBODIMENTS

Figure 1:
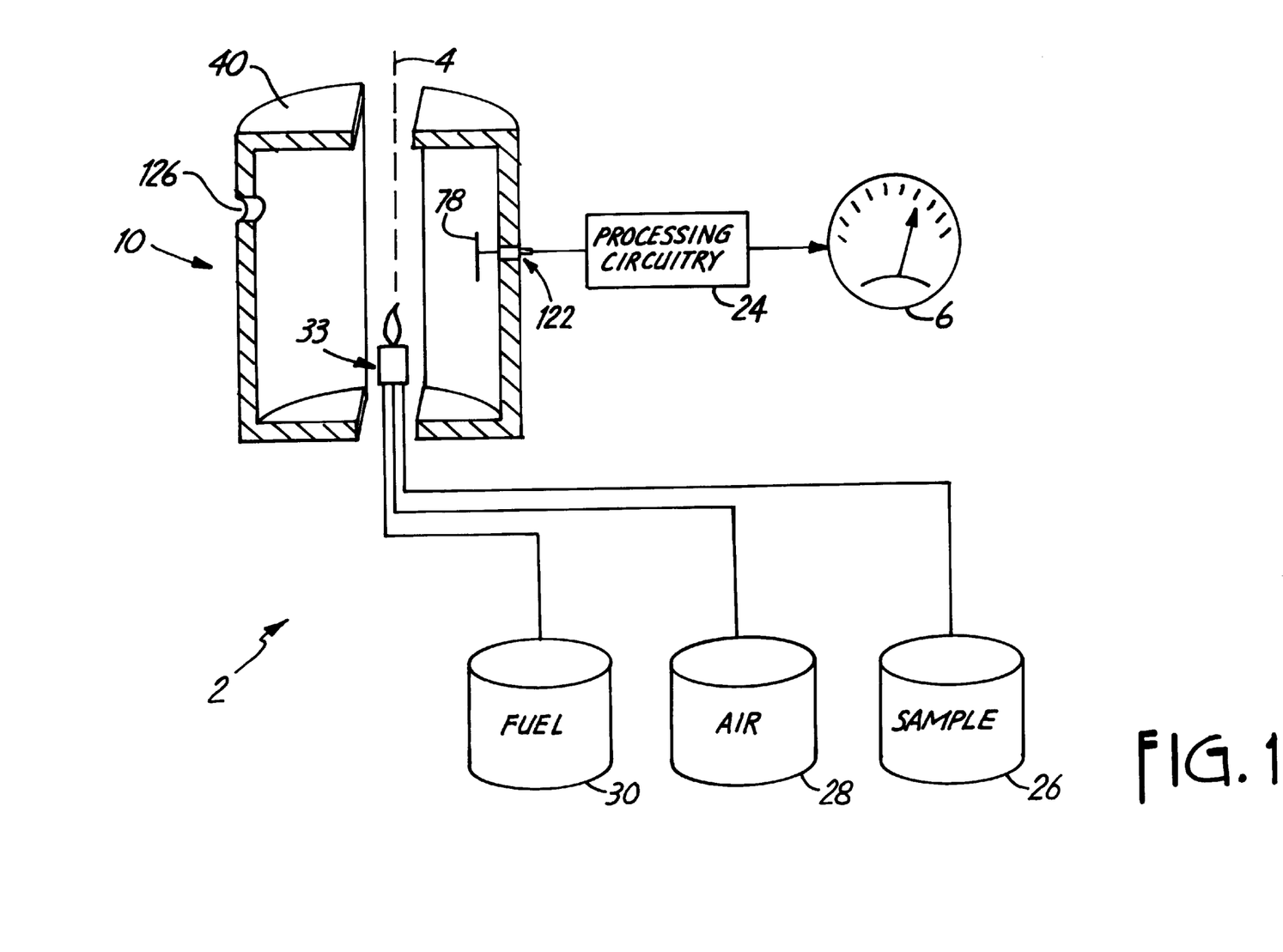
FIG. 1 is a block diagram of a flame ionization detector in accordance with one aspect of the resent invention.

FIG. 1 is a simplified diagram of analyzer 2 including flame ionization detector 10 shown in cross section in accordance with the present invention. Analyzer 2 includes processing or analysis electronics 24, gauge 6, gas sample source 26, air source 28, and fuel source 30. Detector 10 includes ion collector 78, burner 33 and housing 40. Housing 40 is joined together along longitudinal axis 4. Collector 78 is electrically coupled to circuitry 24 by pin 122 which extends through housing 40. A gas sample is provided from sample source 26 and past a flame at burner 33 and out exhaust passage 126. The sample may be, for example, methane gas. Assembly 12 also preferably includes an appropriate valve configuration and a controllable flow regulator for tightly regulating the flow of sample and carrier gas therethrough. In one embodiment, the sample inlet assembly 12 implements a sample gas chromatographic technique. A slug of the sample gas is provided in a carrier gas stream and passed through a column containing a material that absorbs gases at rates proportional to the molecular weight of the gas. The slug of sample gas is therefore separated into its constituents, the lighter components coming through the column prior to the heavier components. Air is provided from air source 28 and fuel is provided from fuel source 30. The fuel is preferably hydrogen or a hydrogen/diluent mixture. Assemblies 14 and 16 include low volume capillaries or conduits for introduction of the air and fuel, respectively. The conduits are coupled through a valve system for selective introduction of the air and fuel to burner 33 for combustion.

Ion collector 78 is arranged proximate the flame generated by ignition of the air and fuel mixture at burner 33. Collector 78 includes polarized electrodes which collect the ions produced as the sample gas passes through the flame. Collection of the ions causes an ionization current to flow through processing or analyzing electronics 24. The current is proportional to the rate at which carbon atoms enter the flame and is therefore a measure of the concentration of hydrocarbons in the sample. Information related to these concentrations may be stored for further analysis or output on a display device such as gauge 6.

Figure 2:
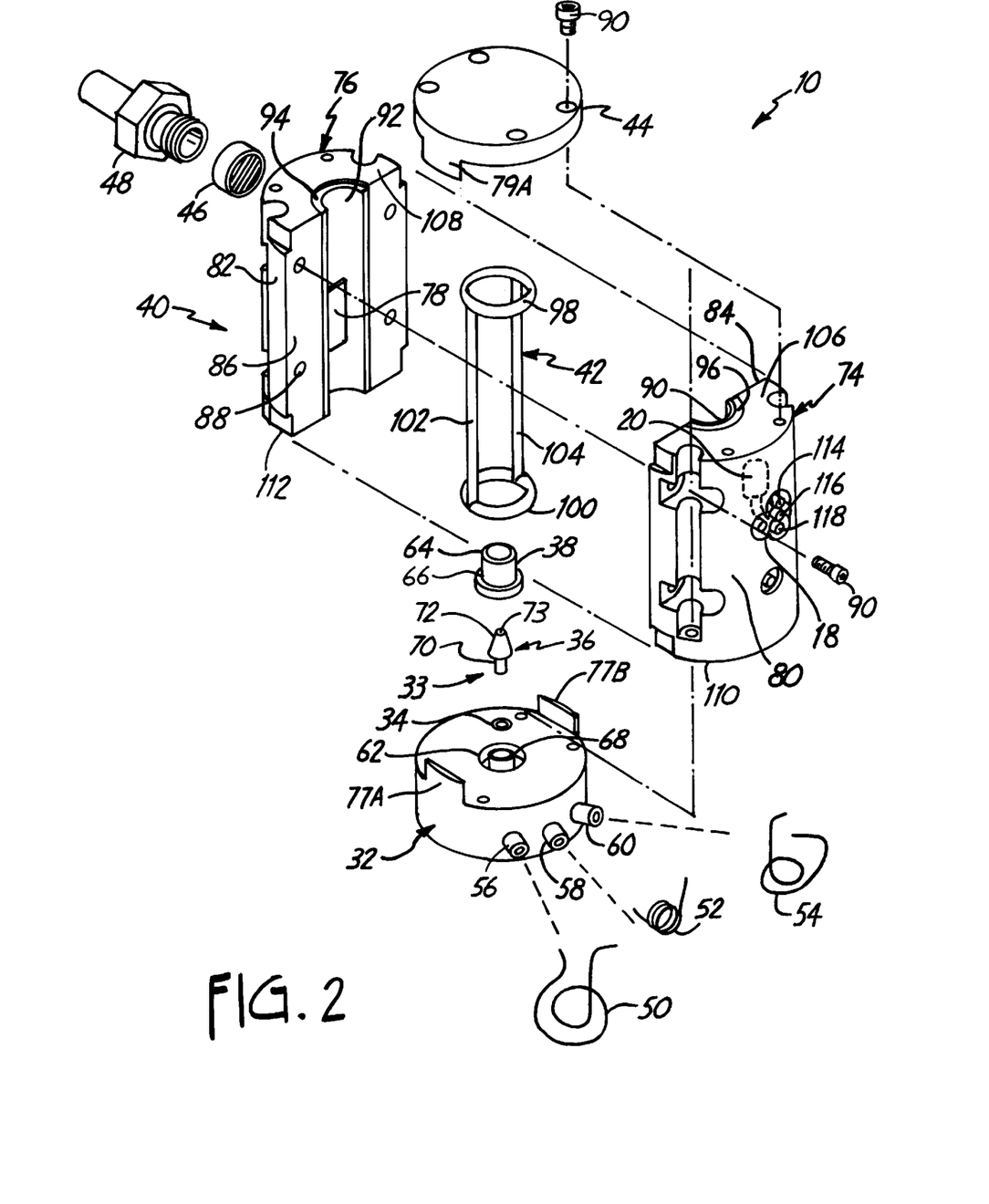
FIG. 2 is an exploded view of a flame ionization detector in accordance with one aspect of the resent invention.

FIG. 2 is an exploded view of flame ionization detector burner 10 in accordance with the present invention. Flame ionization detector 10 includes base 32, burner 33, burner seal 34, flame tip assembly 36, air baffle 38, housing or body portion 40 having a cylindrical flame cavity formed therein, burner seal 42, cap 44, spark arrestor 46, and vent adaptor 48. FIG. 2 also illustrates capillaries 50, 52 and 54 which are coupled to air source 28, fuel source 30, and sample source 26, respectively, shown in FIG. 1. Capillaries 50, 52 and 54 provide conduits to conduct the air, fuel and sample to detector 10. By providing these gases through capillaries, the entire internal volume associated with detector 10 can be kept very small.

Capillaries 50, 52 and 54 are coupled to receiving apertures in receiving assemblies 56, 58 and 60, respectively. Receiving assemblies 56, 58 and 60, in turn, are coupled to passageways within base 32. Base 32 directs the transportation of the fuel gas, air and sample gas, through predefined passages which are preferably machined into base 32. The passages connected to air receiving assembly 56 are coupled to a central region 62 of base 32 where they enter air baffle 38. Air baffle 38 directs the flow of air therethrough in a generally annular ring from a lower portion thereof out annular exit 64 therein. Flow is preferably highly laminar. Air baffle 38 also provides a plurality of pin holes 66 which act to introduce purge air into the inner body of detector 10.

Fuel introduced through fuel receiving assembly 58 passes base 32 and up through an inner central passage 68. Flame tip assembly 36 threadably mates with the interior of central passage 68. Seal 34 is a PTFE seal which is introduced between a shoulder 70 on flame tip assembly 36 and central passage 68. Fuel enters through a lower aperture in flame tip assembly 36 and exits through upper aperture 72 in the center of air baffle 38. Flame tip assembly 36 includes sapphire orifice 73 which forms the central passageway in aperture 72. Sapphire orifice 73 is preferably press fit into the metallic housing of flame tip assembly 36. Sapphire orifice 73 advantageously provides a very precise and smooth hole therethrough which contributes to flame stability. Further, sapphire is substantially corrosion resistant and will maintain the precision hole even when exposed to caustic gasses or wear over extended use.

Flame stability is improved through the use of baffle 38, sapphire orifice 73, pin holes 66, and the relatively small size of the flame cavity (less that 10cc). Improved flame stability is beneficial because it improves the sensitivity of the device. Baffle 38 directs air generally inwardly toward the flame tip assembly 36. Thus, the introduction of the regulated flow of fuel gas through the smooth sapphire orifice 73, and the regulated flow of air surrounding it, and directed toward it, provide a mixture of fuel and air. Pin holes 66 advantageously purge the chamber from the base 32 and promote laminar air flow. A steady flame is thus generated proximate the tip of fuel tip assembly 36 at a point where the fuel and air meet.

Body assembly 40 includes body sections 74 and 76, seal 42, flame arrestor 46, and exhaust adaptor 48. Sections 74 and 76 are preferably of an electrical and thermal insulator, such as plastic. Electrical resistivity reduces leakage of electrical current from ion collector plates 78. Thermal insulation allows detector 10 to be placed in a smaller area with reduced insulation requirements. Body assembly 40 includes a air of ion collector plates 78 (only one of which is shown in FIG. 2, the other being oppositely disposed on body section 74); ignitor 18 and flame detector 20 shown in FIG. 7).

Body sections 74 and 76 are each formed as a portion of a cylinder having exterior surfaces 80 and 82, and mounting surfaces 84 and 86, respectively. Surfaces 84 and 86 are provided with a plurality of threaded apertures 88. Screws 90 threadably engage apertures 88 to connect body portions 74 and 76 together at mounting surfaces 84 and 86, respectively. When assembled, the pair of oppositely disposed recessed portions 90 and 92 form a generally cylindrical flame cavity which encloses flame tip assembly 36, air baffle assembly 38, ion collector plates 78, ignitor 18 and flame detector 20. The flame cavity is surrounded by grooves 94 and 96. Seal 42 is preferably made of Viton which is available from Parker Seal, P.O. Box 11751, Lexington, Ky. 40512. Seal 42 has upper generally circular portion 98, lower generally circular portion 100, and generally parallel legs 102 and 104 which are connected to circular portions 98 and 100. All of the portions of seal 42 are integrally formed with one another as a unitary member and seal 42 fits into grooves 94 and 96. In another embodiment, each of the individual portions of seal 42 are separate, but are connected to one another to form a unitary member.

Body sections 74 and 76 are each provided with upper surfaces 106 and 108, and lower surfaces 110 and 112, respectively. Surfaces 106–112 are provided with threaded holes aligned with corresponding holes in cap 44 and base 32. Screws 90 are adapted to pass through, and threadably engage, the holes to connect cap 44 and base 32 to body sections 74 and 76. When body sections 74 and 76 are attached to base 32 and cap 44, seal 42 seals substantially the entire internal cavity. The design also advantageously provides relatively long flame paths to prevent passage of flame through body assembly 40. Wings 77A and 77B on base 32 and wing 79A (and an opposed wing which is not shown) on cap 44 cover portions of the seams between sections 74 and 76 to prevent flame passage therepast. This configuration lengthens the flame path in both the radial and longitudinal directions. Further, the internal volume associated with the detector 10 is preferably kept less than 10 cubic centimeters which permits the housing to be formed of a plastic material (such as Thorlon® available from Amoco Polymers, Inc. at 4500 McGinnis Ferry Road, Alpharette, Ga. 30202) pursuant to the CENELEC Standard No. EN 50018. The plastic housing is inexpensive to manufacture through an extrusion process is electrical resistive to reduce leakage of electrical current through the detector and thermally insulating to contain heat within the housing. Therefore, even though detector 10 is in an explosion proof container, it is significantly less expensive than prior art explosion proof containers.

Flame arrestor 46 is press fit into an aperture in body section 76. Flame arrestor 46 is preferably a porous metal made of discrete particles and bonded at their contact points by a sintering process. Flame arrestor 46 provides sufficient mechanical strength to withstand sudden pressure shock, and sufficient heat conduction to assist in extinguishing any flame which approaches flame arrestor 46. Exhaust fitting 48 transports byproducts of the sample gas combustion to outside of the burner body assembly 40. Fitting 48 is attached to the burner body by a suitable threaded connection which is assembled over flame arrestor 46. Exhaust fitting 48 also provides redundant support to flame arrestor 46.

The electrical connection made to ignitor filament 18, flame detector 20 and polarized plates 78 is by electrically conductive pins which are spot welded to the appropriate leads of those items and which are press fit through corresponding holes (such as holes 114, 116 and 118) in body sections 74 and 76. The pins are preferably stainless steel and thus facilitate electrical connections from items in the inner cavity of body assembly 40 to the exterior portion of body sections 74 and 76 as shown in FIG. 5.

Figure 3:
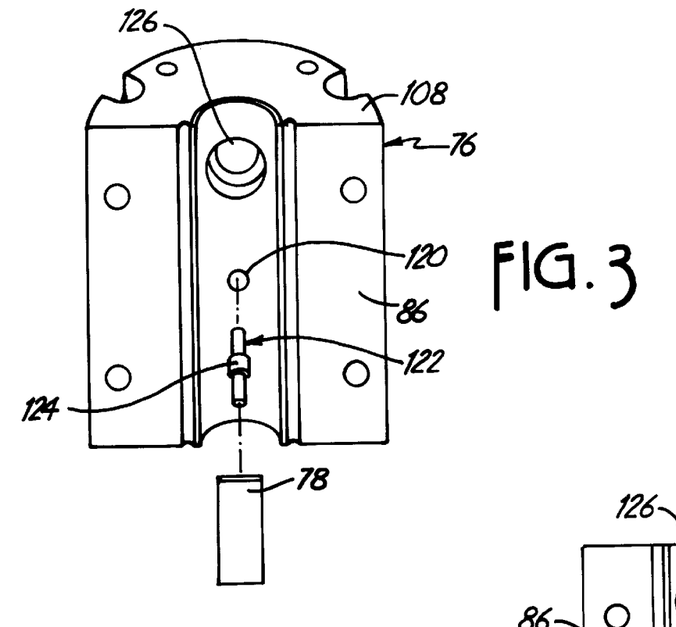
FIG. 3 is a more detailed exploded view of a portion of the flame ionization detector shown in FIG. 2.
Figure 4:
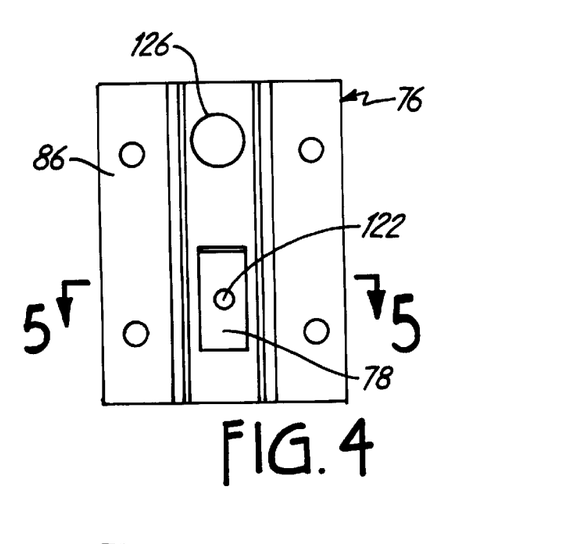
FIG. 4 is an assembled view of the portion shown in FIG. 3.
Figure 5:
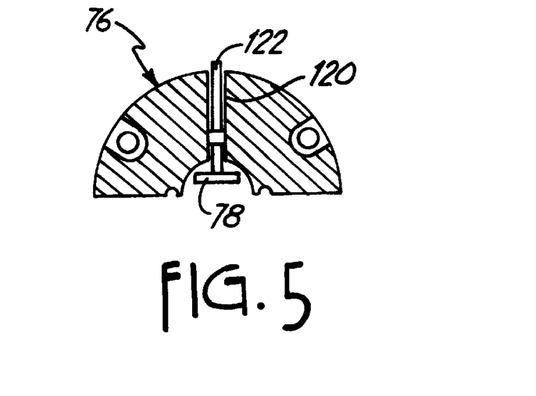
FIG. 5 is a cross-sectional view of the components shown in FIG. 4.

FIGS. 3–7 illustrate the connection of these components in greater detail. FIG. 3 is an exploded view illustrating the assembly of one of polarized collector plates 78 onto body section 76. FIG. 3 illustrates through hole 120 extends from the interior surface to the exterior surface of section 76 Pin 122 has an enlarged diameter portion 124 which is slightly larger than the interior diameter of hole 120. Thus, press fitting pin 122 into hole 120 causes tight frictional engagement between portion 124 and body section 76 to retain pin 122 in hole 120. This design provides a highly reliable connection with a long flame path which tightly seals the flame cavity. Plate 78 is spot welded to the end of pin 122 which provides an electrical connection to and provides support of plate 78. Pin 122 provides electrical connection to plate 78 through body section 76. FIG. 3 also shows exhaust passageway aperture 126 which receives exhaust fitting 48. FIG. 4 shows plate 78 assembled to body section 76 via the press fitting process described with respect to FIG. 4. Pin 122 is shown in phantom in FIG. 4. FIG. 5 is a cross-sectional view taken along section lines 5—5 in FIG. 4. FIG. 5 illustrates how press fitting pin 122 into hole 120, and spot welding plate 78 to pin 120, precisely locates plate 78 through an easy and efficient assembly process.

Figure 6:
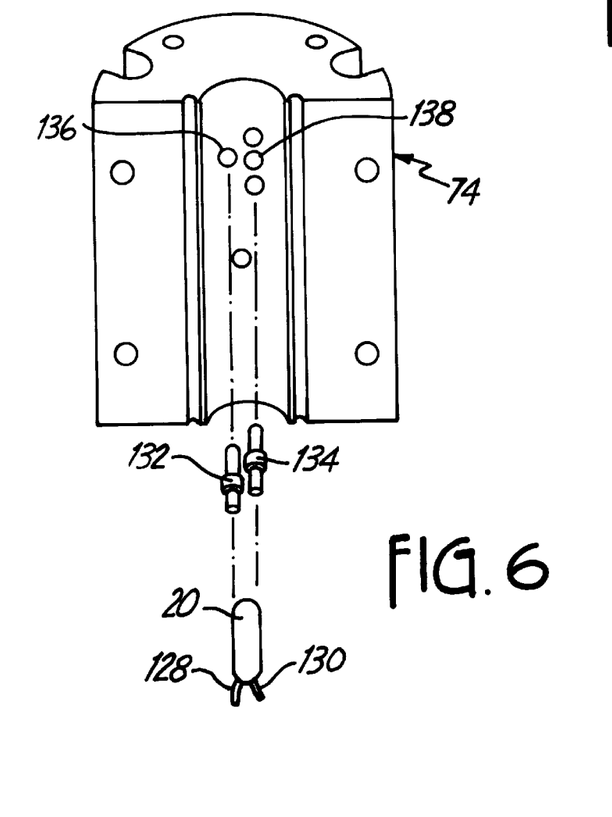
FIG. 6 is a more detailed exploded view of a portion of the flame ionization detector shown in FIG. 2.
Figure 7:
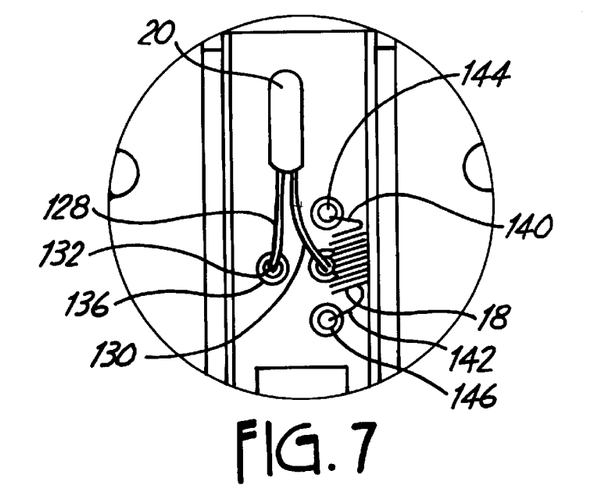
FIG. 7 is an assembled vies of the component shown in FIG. 3.

FIGS. 6 and 7 illustrate the connection of flame detector 20 and ignitor filament 18. Flame detector 20, in one preferred embodiment, is implemented as a thermistor which has a plurality of leads 128 and 130. Leads 128 and 130 are spot welded to pins 132 and 134, respectively. Pins 132 and 134 are press fit into holes 136 and 138 in body section 74. In a preferred embodiment, the thermistor is placed above the exhaust aperture 126 so that the internal temperature of the detector can be measured and monitored. Ignitor coil 18 is preferably positioned just below vent aperture 126 so that an easy ignition can be made. Coil 18 also has a pair of leads 140 and 142 which are spot welded to pins 144 and 146. Pins 144 and 146 are, in turn, press fit into apertures in body section 74 to provide electrical connection from the inner cavity defined by body sections 74 and 76 to the exterior thereof.

Figure 8:
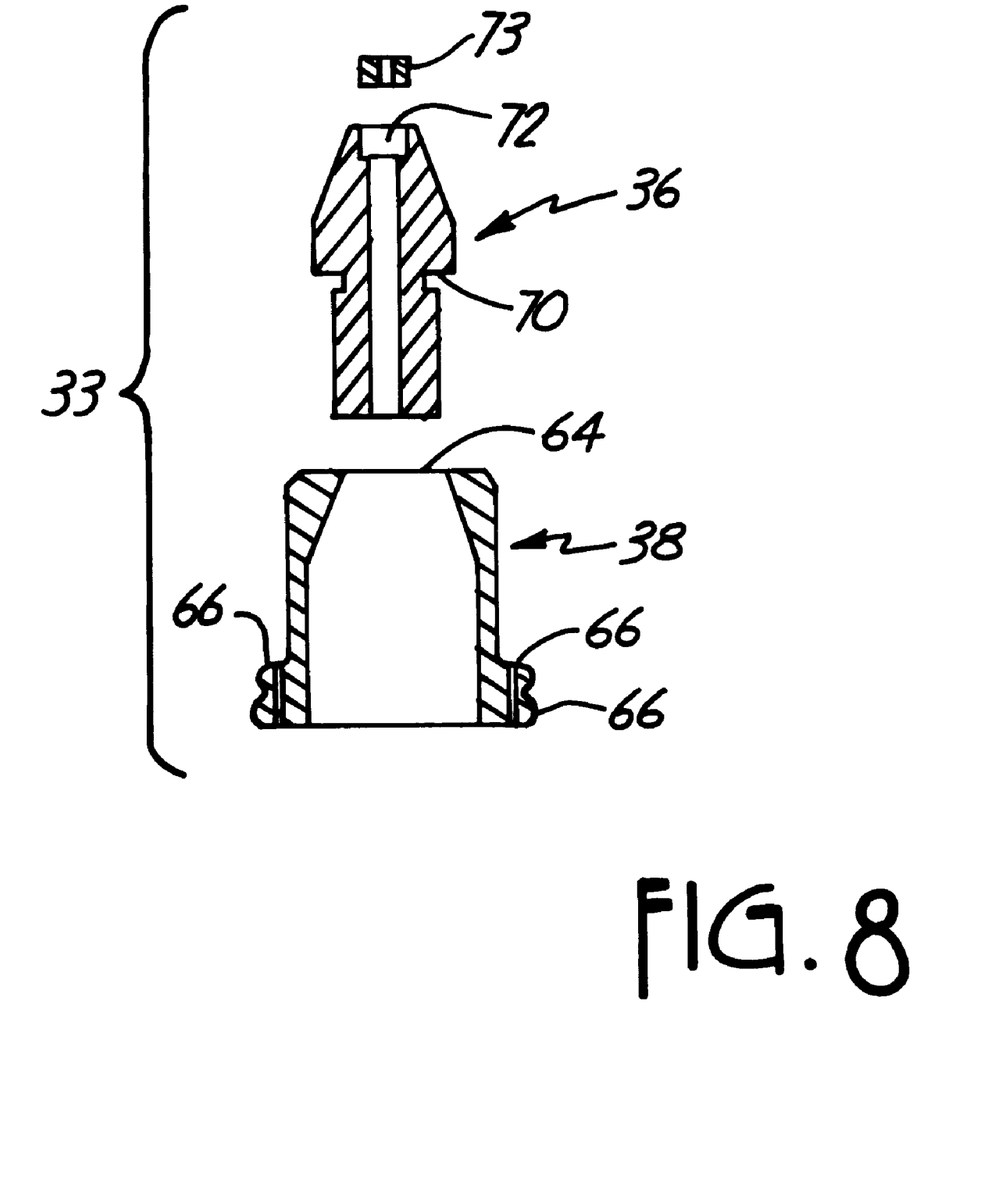
FIG. 8 is an exploded cross-sectional view of a burner of FIG. 2.

FIG. 8 is an exploded cross-sectional view of burner 33 showing the relationship between baffle 38. flame tip 36 and sapphire orifice 72. Sapphire orifice 72 has a diameter of 0.094 inches, a thickness of 0.063 inches and includes passageway 148 having a diameter of 0.015 inches and may be obtained from Bird Precision, of P.O. Box 569, Waltham, Mass. 02254. Orifice 73 is press fit in aperture 72 and tip 36 and baffle 38 are threaded into base 32 of FIG. 2. In one preferred embodiment, four evenly pin holes 66 are evenly spaced at ninety degree increments around flange 66.

Figure 9:
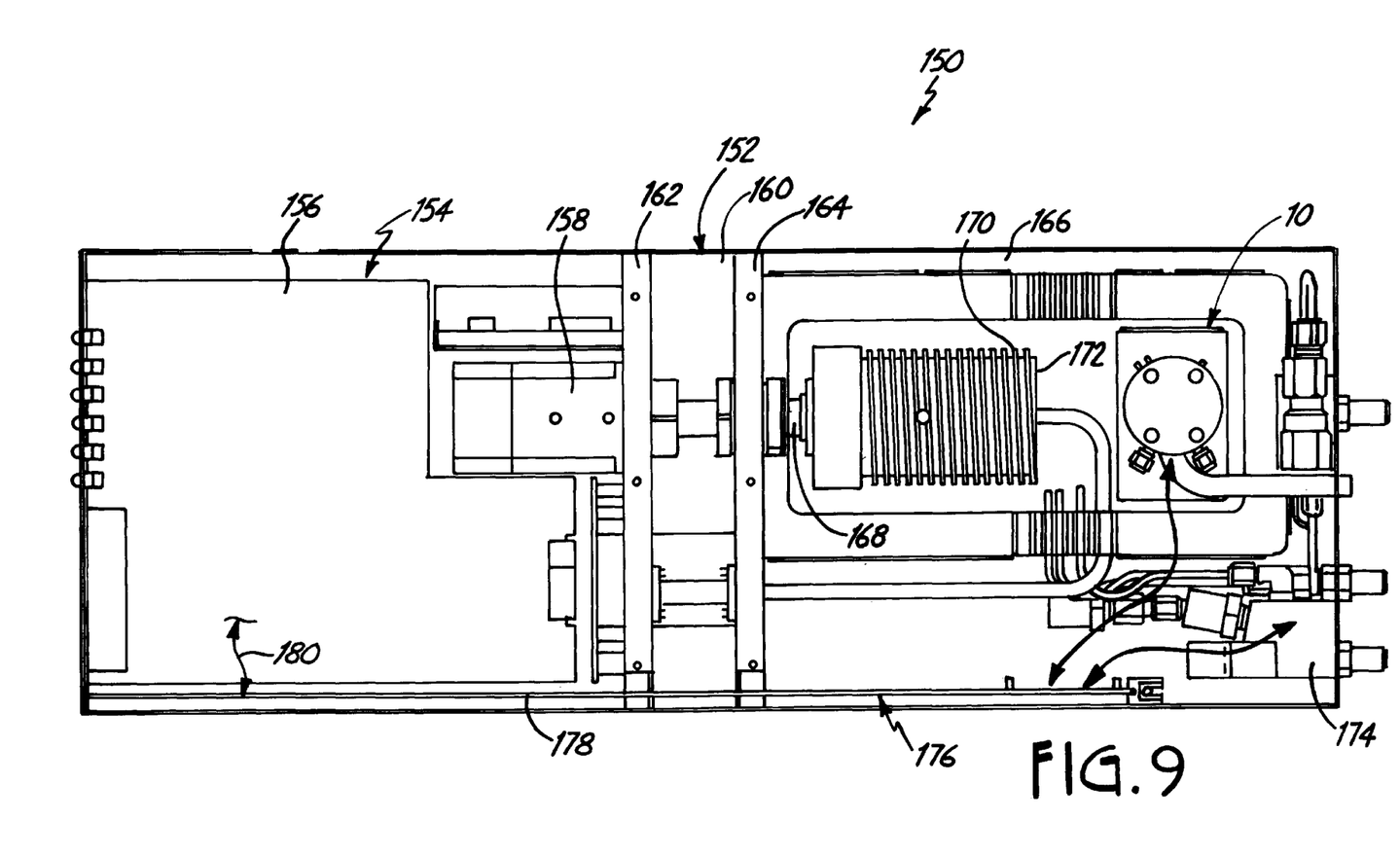
FIG. 9 is a top view illustrating the flame ionization detector disclosed in FIG. 2 as used in a hydrocarbon analyzer in accordance with another aspect of the present invention.

FIG. 9 illustrates the implementation of flame ionization detector 10 in hydrocarbon analyzer 150 which includes housing 152 having three chambers. The design also provides a small profile such that the detector may be used in multiple applications such as analyzer 150. Electronics chamber 154 houses a vertically mounted printed circuit board 156 containing processing and power supply circuitry. Chamber 154 also includes valve actuator 158 which actuates a valve controlling flow of gas through analyzer 150. Central isolation chamber 160 is formed by bulkheads 162 and 164 coupled to provide a physical separation between electronics chamber 154 and a pneumatics chamber 166. Bulkheads 162 and 164 are preferably metal plates connected within housing 152 to form isolation zone 160 and act to prevent any gas leaks in pneumatic chamber 166 from reaching electronics chamber 154. Isolation chamber 160 provides an. additional buffer between the electronics and the detector 10.

Chamber 166 includes valve 168 which is coupled to valve actuator 158, heater manifold 170, flame ionization detector 10 and column configurations 172. Chamber 166 is preferably a thermally controlled insulated enclosure having a temperature maintained at, for example, 120° C. which allows the instrument to measure certain hydrocarbons without. difficulty. Chamber 166 includes regulator valves 174, preferably fluistors, which are microprocessor controlled, electrically set valves formed in silicon. The valves are used to control pressure instead of conventional pressure regulators.

Electrical connections between electronics chamber 154 and pneumatic chamber 166 are preferably provided by electronic connection assembly 176. In a preferred embodiment, electronic connection assembly 176 includes a printed circuit board 178 which extends from electronics chamber 154, through isolation zone 160 and into pneumatic chamber 166. Printed circuit board 178 preferably contains electrically conductive traces, which are current limited and voltage limited (or power limited) by over-voltage protection devices and current limiting resistors. This prevents power dissipation in pneumatic chamber 166 which could provide an ignition source to any volatile gas which resides in chamber 166. The traces on printed circuit board 178 are preferably coupled to appropriate circuits on circuit board 156, as indicated by arrow 180. Also, the traces are preferably coupled in pneumatic chamber 166 to control fluistors 174, flame ionization detector 10, and any other suitable devices which require electronic manipulation or control by the circuitry in chamber 154.

By separating the electronics chamber from the pneumatic chamber, and by providing the flame ionization detector in an explosion proof container, significant problems associated with implementing a flame ionization detector in a volatile environment are overcome. The electrical connections between the electronics chamber and the pneumatic chamber are provided in a power limiting fashion such that the connections cannot dissipate enough power to provide an ignition source.

The present invention provides the flame ionization detector of the invention can be disassembled in a highly efficient manner and provides for the placement and assembly of parts in the detector in a highly accurate and efficient manner. The invention may be used in explosion proof, or non-explosion proof designs.

Although the present invention has been described with reference to preferred embodiments, workers skilled in the art will recognize that changes may be made in form and detail without departing from the spirit and scope of the invention.

What is claimed is:

1. A flame ionization detector burner, comprising:
  a housing having a flame cavity therein having a length extending along a generally longitudinal axis of the housing and a housing exterior with intake passageways communicating between the housing exterior and the flame cavity for passing fuel, air and sample flows into the flame cavity and an exhaust passage communicating between the housing exterior and the flame cavity for passing exhaust gasses out of the flame cavity;
  a burner carried in the flame cavity receiving the fuel, air, and sample flow generating a flame to ionize the sample;
  an ion collector plate spaced away from the burner carried in the flame cavity collecting sample ions and providing an electrical output representative of the sample ions to the housing exterior via an electrical feedthrough between the flame cavity and the housing exterior; and
  the housing further comprises at least two sidewalls removably joined together along the generally longitudinal axis of the housing and in a direction of the length of the flame cavity.

2. The flame ionizer detector burner of claim 1 wherein the electrical feedthrough comprises an elongated electrically conductive pin extending through the housing and electrically connected to the ion collector plate.

3. The flame ionization detector burner of claim 2 wherein the housing includes an aperture and the pin is press fit into the aperture.

4. The flame ionization detector burner of claim 1 wherein opposing ends of the housing are sealed by a cap and a base.

5. The flame ionization detector burner of claim 4 and further comprising:
 a cap seal disposed adjacent a cap connection surface on the housing proximate the cap;
 a base seal disposed adjacent a base connection surface on the housing proximate the base; and
 a sidewall seal disposed adjacent the sidewalls.

6. The flame ionization detector burner of claim 5 wherein the cap seal, the base seal and the sidewall seal are connected together to form a unitary member.

7. The flame ionization detector burner of claim 6 wherein the cap seal and the base seal are disposed generally concentrically about the longitudinal axis of the housing and wherein the sidewall seal is disposed generally parallel to the longitudinal axis.

8. The flame ionization detector burner of claim 1 wherein the housing comprises an electrically insulating material.

9. The flame ionization detector burner of claim 8 wherein the housing comprises a plastic.

10. The flame ionization detector burner of claim 9 wherein the flame cavity has a volume of less than approximately ten cubic centimeters.

11. The flame ionization detector burner of claim 1 and further comprising:
 an exhaust outlet including an aperture in housing; and
 a spark arrestor assembly press fit into the aperture.

12. The flame ionization detector burner of claim 1 and further comprising:
 a flame detector mounted within the flame cavity.

13. The flame ionization detector burner of claim 1 wherein flame paths through the detector are elongated in both the longitudinal and radial directions.

14. The flame ionization detector burner of claim 13 including wings extending over at least a portion of the sidewalls to provide a lengthened flame path therepast.

15. The flame ionization detector burner of claim 14 wherein the wings extend from caps sealingly coupled to opposing ends of the housing.

16. The flame ionization detector burner of claim 1 wherein the housing comprises:
 a first member having a shape generally in the form of a half cylinder; and
 a second member having a shape generally in the form of a half cylinder.

17. The flame ionization detector burner of claim 1 wherein the burner includes an orifice formed of sapphire carrying the sample flow therethrough.

18. The flame ionization detector burner of claim 1 including a baffle proximate the flame to promote laminar flow of the air.

19. The flame ionization detector burner of claim 18 wherein the baffle includes a flange having at least one hole formed therein to purge the flame cavity with the air.

20. The flame ionization detector burner of claim 19 wherein the flange is located proximate one end of the flame cavity.

21. The flame ionization detector burner of claim 1 wherein the flame cavity is generally cylindrical and extends along the generally longitudinal axis of the housing.

22. A hydrocarbon analyzer, comprising:
 a housing having a first chamber, a second chamber and an isolation chamber, the isolation chamber being disposed between the first and second chambers and defined by first and second wall portions within the housing;
 an electronic analyzer circuit disposed in the first chamber; and
 a flame ionization detector burner as set forth in claim 1 disposed in the second chamber and wherein the electronic analyzer circuit couples to the ion collector plate.

23. A flame ionization detector burner, comprising:
 a housing having a flame cavity formed therein extending along a generally longitudinal axis of the housing and a housing exterior with intake passageways communication between the housing exterior and the flame cavity for passing fuel, air and sample flows into the flame cavity and an exhaust passage communication between the housing exterior and the flame cavity for passing exhaust gasses out of the flame cavity;
 a burner carried in the housing cavity receiving the fuel, air, and sample flow generating a flame to ionize the sample, the burner including a trip;
 an ion collector carried in the flame cavity collecting sample ions and providing an electrical output representative of the sample ions to the housing exterior via an electrical feedthrough between the flame cavity and the housing exterior; and
 the housing further comprising a baffle around the flame tip of the burner to promote substantially laminar air flow.

24. The flame ionization detector burner of claim 23 wherein the baffle includes a flange having at least one pin hole therein to purge the flame cavity with the air.

25. The flame ionization detector burner of claim 23 wherein the burner further includes an orifice formed of sapphire.

26. A flame ionization detector burner, comprising:
 housing means for providing a flame cavity therein extending along a generally longitudinal axis of the housing means and a housing exterior with intake passageways communicating between the housing exterior and the flame cavity for passing fuel, air and sample flows into the flame cavity and an exhaust passage communicating between the housing exterior and the flame cavity for passing exhaust gasses out of the flame cavity;
 burner means carried in the housing cavity for receiving the fuel, air, and sample flow and generating a flame at a flame tip to ionize the sample;
 ion collector means carried in the flame cavity collecting sample ions and providing an electrical output representative of the sample ions to the housing exterior via an electrical feedthrough between the flame cavity and the housing exterior; and
 means around the flame tip for promoting a substantially laminar air flow proximate the burner means.

\* \* \* \* \*

UNITED STATES PATENT AND TRADEMARK OFFICE
CERTIFICATE OF CORRECTION

| | |
|---|---|
| PATENT NO. | : 6,238,622 B1 |
| DATED | : May 29, 2001 |
| INVENTOR(S) | : Shahram M. Salimian |

It is certified that error appears in the above-identified patent and that said Letters Patent is hereby corrected as shown below:

<u>Title page,</u>
Item [57], ABSTRACT,
Line 12, change "time" to -- flame --.

<u>Column 8,</u>
Lines 18-19, change "communication" to -- communicating --.
Line 21, change "communication" to -- communicating --.

Signed and Sealed this

Nineteenth Day of March, 2002

*Attest:*

JAMES E. ROGAN
*Director of the United States Patent and Trademark Office*

*Attesting Officer*